United States Patent
Firstenberg et al.

(10) Patent No.: US 9,808,251 B2
(45) Date of Patent: Nov. 7, 2017

(54) TISSUE RESECTION DEVICES AND RELATED METHODS

(71) Applicant: Boston Scientific Scimed, Inc., Maple Grove, MN (US)

(72) Inventors: Laura Elizabeth Firstenberg, Worcester, MA (US); Colby Harris, Weston, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 707 days.

(21) Appl. No.: 14/461,857

(22) Filed: Aug. 18, 2014

(65) Prior Publication Data

US 2015/0066046 A1    Mar. 5, 2015

Related U.S. Application Data

(60) Provisional application No. 61/871,063, filed on Aug. 28, 2013.

(51) Int. Cl.
*A61B 17/12* (2006.01)
*A61B 17/3205* (2006.01)
(Continued)

(52) U.S. Cl.
CPC ........ *A61B 17/12* (2013.01); *A61B 17/32056* (2013.01); *A61B 18/1492* (2013.01);
(Continued)

(58) Field of Classification Search
CPC ...... A61B 17/32053; A61B 17/320758; A61B 17/320783; A61B 17/12009;
(Continued)

(56) References Cited

U.S. PATENT DOCUMENTS 3,181,533 A * 5/1965 Heath ............... A61B 17/26
606/113
5,066,295 A * 11/1991 Kozak ............... A61B 18/14
606/47

(Continued)

FOREIGN PATENT DOCUMENTS

| EP | 1691695 B1 | 7/2007 |
| WO | WO 2004/052594 A2 | 6/2004 |
| WO | WO 2006/122279 A2 | 11/2006 |

OTHER PUBLICATIONS

International Search Report and Written Opinion of the International Searching Authority in International Application No. PCT/US2014/051476, mailed Nov. 5, 2014, 15 pages.

*Primary Examiner* — Matthew F Desanto
(74) *Attorney, Agent, or Firm* — Bookoff McAndrews, PLLC

(57) ABSTRACT

A medical device is disclosed which includes a delivery member having at least two lumens extending within. Each lumen may include a rotational element within. Each rotational element may be configured to convert linear motion into rotational motion. The medical device may also include a snare element including a distal snare loop and two proximally extending legs. Each leg of the snare element may be within one of the two lumens. Further, the rotational element in a first lumen may be configured to impart a clock-wise rotation to a first leg of the two proximally extending legs, while the rotational element in a second lumen of the at least two lumens may be configured to impart a counter clock-wise rotation to a second leg of the two proximally extending legs.

17 Claims, 11 Drawing Sheets

(51) Int. Cl.
  *A61B 18/14* (2006.01)
  *A61B 17/00* (2006.01)
  *A61B 18/00* (2006.01)

(52) U.S. Cl.
  CPC ............ *A61B 2017/00269* (2013.01); *A61B 2018/00107* (2013.01); *A61B 2018/00166* (2013.01); *A61B 2018/00214* (2013.01); *A61B 2018/141* (2013.01); *A61B 2018/1465* (2013.01)

(58) Field of Classification Search
  CPC .... A61B 2017/2923; A61B 2017/2924; A61B 17/221; A61B 2017/2217; A61B 2017/2212; A61B 17/32056; A61B 17/26
  USPC ........................................................ 606/113
  See application file for complete search history.

(56) References Cited

U.S. PATENT DOCUMENTS

| | | | | |
|---|---|---|---|---|
| 5,163,942 A * | 11/1992 | Rydell | ............ | A61B 17/32056 606/1 |
| 6,352,539 B1 * | 3/2002 | Avellanet | ......... | A61B 17/32056 606/110 |
| 6,773,432 B1 * | 8/2004 | Clayman | .......... | A61B 17/32056 606/113 |
| 7,306,587 B2 * | 12/2007 | O'Sullivan | ............ | A61B 18/14 606/1 |
| 8,092,470 B2 * | 1/2012 | Miyamoto | ............. | A61B 17/22 606/114 |
| 9,107,691 B2 * | 8/2015 | Fojtik | ............ | A61B 17/320758 |
| 9,155,551 B2 * | 10/2015 | Kuroda | ................ | A61B 17/221 |
| 2002/0010485 A1 * | 1/2002 | Griego | ............ | A61B 17/32056 606/167 |
| 2003/0109889 A1 * | 6/2003 | Mercereau | ........... | A61B 17/221 606/127 |
| 2004/0092953 A1 * | 5/2004 | Salameh | .......... | A61B 17/32056 606/113 |
| 2005/0119668 A1 * | 6/2005 | Teague | ................. | A61B 17/221 606/127 |
| 2005/0182433 A1 * | 8/2005 | Nady | ..................... | A61B 17/22 606/170 |
| 2007/0260264 A1 * | 11/2007 | Nobis | .............. | A61B 17/32056 606/113 |
| 2008/0086854 A1 * | 4/2008 | Boyd | .................. | A61B 17/064 24/715.3 |
| 2009/0069806 A1 * | 3/2009 | De La Mora Levy | .................... | A61B 17/221 606/46 |
| 2010/0217151 A1 * | 8/2010 | Gostout | ............ | A61B 1/00094 600/565 |
| 2010/0234862 A1 * | 9/2010 | Patel | ................ | A61B 17/12009 606/151 |
| 2010/0331883 A1 * | 12/2010 | Schmitz | ............. | A61B 10/0275 606/249 |
| 2011/0106077 A1 * | 5/2011 | Yanuma | ........... | A61B 17/32056 606/45 |
| 2011/0245827 A1 * | 10/2011 | Okada | .................... | A61B 17/29 606/41 |
| 2011/0313529 A1 * | 12/2011 | Schaller | ........... | A61B 17/32002 623/17.16 |
| 2012/0172662 A1 * | 7/2012 | Kappel | ................ | A61B 17/221 600/104 |
| 2012/0172864 A1 | 7/2012 | Farin et al. | | |
| 2012/0323262 A1 * | 12/2012 | Ibrahim | ........... | A61B 17/12013 606/144 |
| 2013/0131688 A1 * | 5/2013 | Schwartz | ............. | A61B 17/221 606/113 |
| 2013/0158566 A1 | 6/2013 | Harris et al. | | |
| 2013/0268063 A1 | 10/2013 | Firstenberg et al. | | |
| 2013/0296918 A1 * | 11/2013 | Johnson | .................... | A61F 2/01 606/200 |
| 2015/0032119 A1 * | 1/2015 | Kuroda | ................ | A61B 17/221 606/113 |
| 2015/0066046 A1 * | 3/2015 | Firstenberg | ............ | A61B 17/12 606/113 |

\* cited by examiner

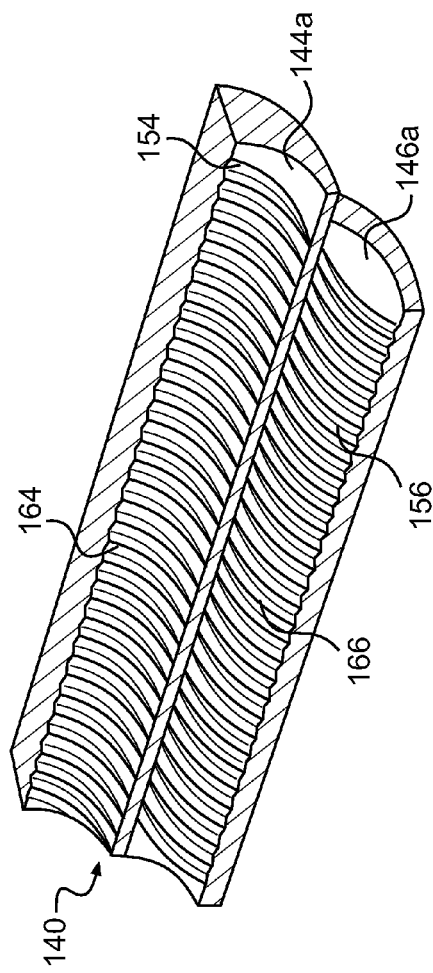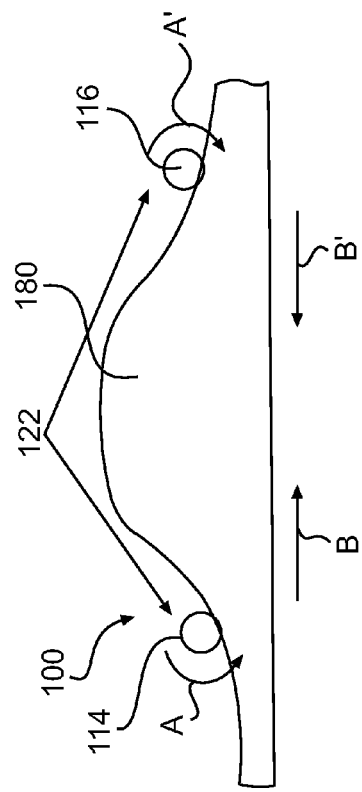

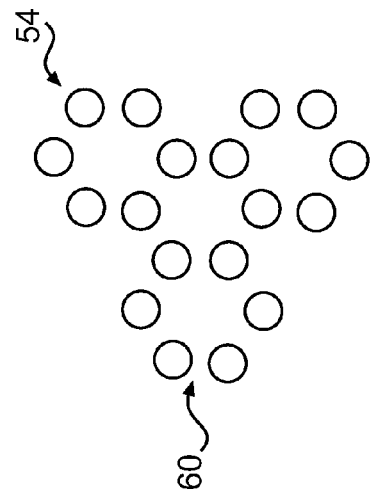
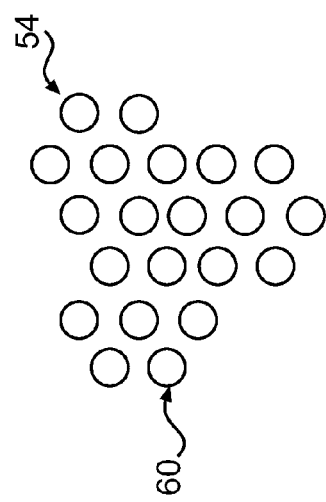
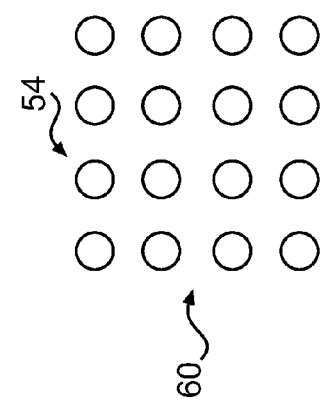
FIG. 8C
FIG. 8B
FIG. 8A

TISSUE RESECTION DEVICES AND RELATED METHODS

CROSS REFERENCE TO RELATED APPLICATIONS

This application claims the benefit of U.S. Provisional Application No. 61/871,063, filed Aug. 28, 2013, the disclosure of which is incorporated herein by reference in its entirety.

FIELD OF THE INVENTION

Embodiments of the present disclosure relate to medical devices and procedures. In particular, embodiments of the present disclosure relate to medical devices and methods for tissue resection.

BACKGROUND OF THE INVENTION

A variety of minimally invasive instruments and related techniques have been developed for diagnosis and treatment of various ailments and conditions. Endoscopic procedures, such as Endoscopic Mucosal Resection (EMR), Endoscopic Sub-mucosal Resection (ESR), Polypectomy, Mucosectomy, etc., are minimally invasive methods for removal of abnormal or diseased tissue from a patient's body.

For example, a physician may excise sessile adenomas (i.e., tumors attached to a bodily surface) from the colon or other parts of the gastrointestinal tract using EMR. Minimally-invasive instruments may be inserted into a body lumen and used for resecting the target tissue while leaving the underlying tissue plane intact. Instruments like snares with a loop portion may be used to ensnare or surround the target tissue and resect it by tightening the snare and/or by energizing the snare and pulling the snare so as to cut the tissue.

A physician's ability to control the snare is an important factor that determines its effectiveness for resection. When a physician places a snare on the target tissue, many conventional snares have a tendency to slip off the tissue to be resected. Such snares may be unable to sufficiently grip the tissue and may require repeated efforts to capture the target tissue. If the physician is not able to properly control the snare, the target tissue may not be properly captured and resected. Improper placement of the snare may also lead to an irregular cut, or an angled cut and cause damage to the surrounding tissue. As a result, there may be unnecessary loss of blood and healthy tissue from a patient's body, which may further lead to difficulties in visualization and patient recovery.

Therefore, there exists a need for devices and methods that offer physicians better control to grip tissue effectively for consistent capture, excision, or removal of unwanted tissue without affecting the surrounding tissue.

SUMMARY OF THE INVENTION

Embodiments of the present disclosure relate to medical devices and methods for performing resection of abnormal or diseased tissue.

According to embodiments of the present disclosure, a medical device may include delivery member having at least two lumens extending therethrough. Each lumen of the at least two lumens may include a rotational element therein. Each rotational element may be configured to convert linear motion into rotational motion. The medical device may further include a snare element including a distal snare loop and two proximally extending legs. Each leg may be within one of the at least two lumens. The rotational element in a first lumen of the at least two lumens may be configured to impart a clock-wise rotation to a first leg of the two proximally extending legs. Additionally, the rotational element in a second lumen of the at least two lumens may be configured to impart a counter clock-wise rotation to a second leg of the two proximally extending legs.

The medical device may further include one or more of the following features: a plurality of micro-features extending radially outwardly from the snare element; an adhesive coating extending along at least a portion of the snare element; the rotational element in each of the at least two lumens may include at least one of a female helical groove and a helical mandrel; the adhesive coating may include at least one of a pressure sensitive adhesive material and a mucoadhesive material; the adhesive coating may be disposed on the snare loop; at least one of the plurality of micro-features may extend at an angle non-perpendicular to a base of the snare element; and at least one of the plurality of micro-features may be a selectively deployable flap.

According to further embodiments of the present disclosure a medical device may include a delivery member having at least two lumens extending therethrough. Each lumen of the at least two lumens may include a rotational element therein. Each rotational element may be configured to convert linear motion into rotational motion. The medical device may further include a snare element including a distal snare loop and two proximally extending legs. Each leg may be within one of the at least two lumens. The snare loop may include a first side wire portion and a second side wire portion opposite the first side wire portion on opposite sides of a longitudinal axis of the snare element, and wherein application of an axial force to the proximally extending legs may cause clock-wise rotation of the first side wire portion about an axis of the first side wire portion and may cause counter clock-wise rotation of the second side wire portion about an axis of the second side wire portion.

The medical device may further include one or more of the following features: an adhesive coating extending along at least a portion of the snare element, wherein the adhesive coating may include at least one of a pressure sensitive adhesive material and a mucoadhesive material; wherein the rotational element in each of the at least two lumens may include at least one of a female helical groove and a helical mandrel; the rotational element in a first lumen of the at least two lumens may be right-handed, and wherein the rotational element in a second lumen of the at least two lumens may be left-handed; a plurality of micro-features may extend radially outwardly from the snare element; and at least one of the plurality of micro-features may include a selectively deployable flap.

According to further embodiments of the present disclosure, a method of operating a medical device may include deploying a snare about tissue of a patient. The snare may include a delivery member having at least two lumens extending therethrough. Each lumen of the at least two lumens may include a rotational element therein. Each rotational element may be configured to convert linear motion into rotational motion. A snare element may include a distal snare loop and two proximally extending legs. Each leg may be within one of the at least two lumens. The snare loop may include a first side wire portion and a second side wire portion opposite the first side wire portion on opposite sides of a longitudinal axis of the snare element. The method may further include applying an axially directed force so as to impart clock-wise rotation of the first side wire portion about an axis of the first side wire portion and counter clock-wise rotation of the second side wire portion about an axis of the second side wire portion.

The method may further include one or more of the following features: engaging tissue via a plurality of micro-features extending radially outwardly from the snare element; where the applying may include pulling on a proximal end of the legs or moving a sheath disposed about the loop proximally; where the engaging may include forming a directional engagement with tissue, wherein at least one of the plurality of micro-features may extend at an angle non-perpendicular to a base of the snare element; snare element may include an adhesive coating extending along at least a portion of the snare element, the adhesive coating including at least one of a pressure sensitive adhesive material and a mucoadhesive material; and the rotational element in each of the at least two lumens may include at least one of a female helical groove and a helical mandrel.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary embodiments of the present disclosure and together with the description, serve to explain the principles of the disclosure.

FIG. 2 is a cut-away view of the exemplary medical device of FIG. 1;

FIG. 3 is a schematic illustration of an exemplary medical device in use;

FIGS. 7A-7B and 8A-8C show exemplary micro-patterns of micro-features on embodiments of the snare element;

DESCRIPTION OF THE EMBODIMENTS

Reference will now be made in detail to embodiments of the present disclosure, examples of which are illustrated in the accompanying drawings. Wherever possible, the same reference numbers will be used throughout the drawings to refer to the same or like parts. The term "distal" refers to the direction that is away from the user and into the patient's body. By contrast, the term "proximal" refers to the direction that is closer to the user and away from the patient's body.

Overview

Embodiments of the present disclosure relate to medical devices for resecting and/or retrieving undesired tissue such as, for example, cancerous tissue or lesions within a patient's body. For example, tissue disposed on, e.g., the mucosal walls of the colon, esophagus, stomach, and/or duodenum can be resected to treat a patient. A physician may also resect tissue in order to conduct a biopsy or other examination. It should be noted that medical devices presented in this disclosure can be used for both resecting and retrieving a target tissue. Additionally, devices and methods according to this disclosure may be used to treat any body tissue desired, for example, tissue located within the gastrointestinal tract.

Exemplary Embodiments

Figure 1:
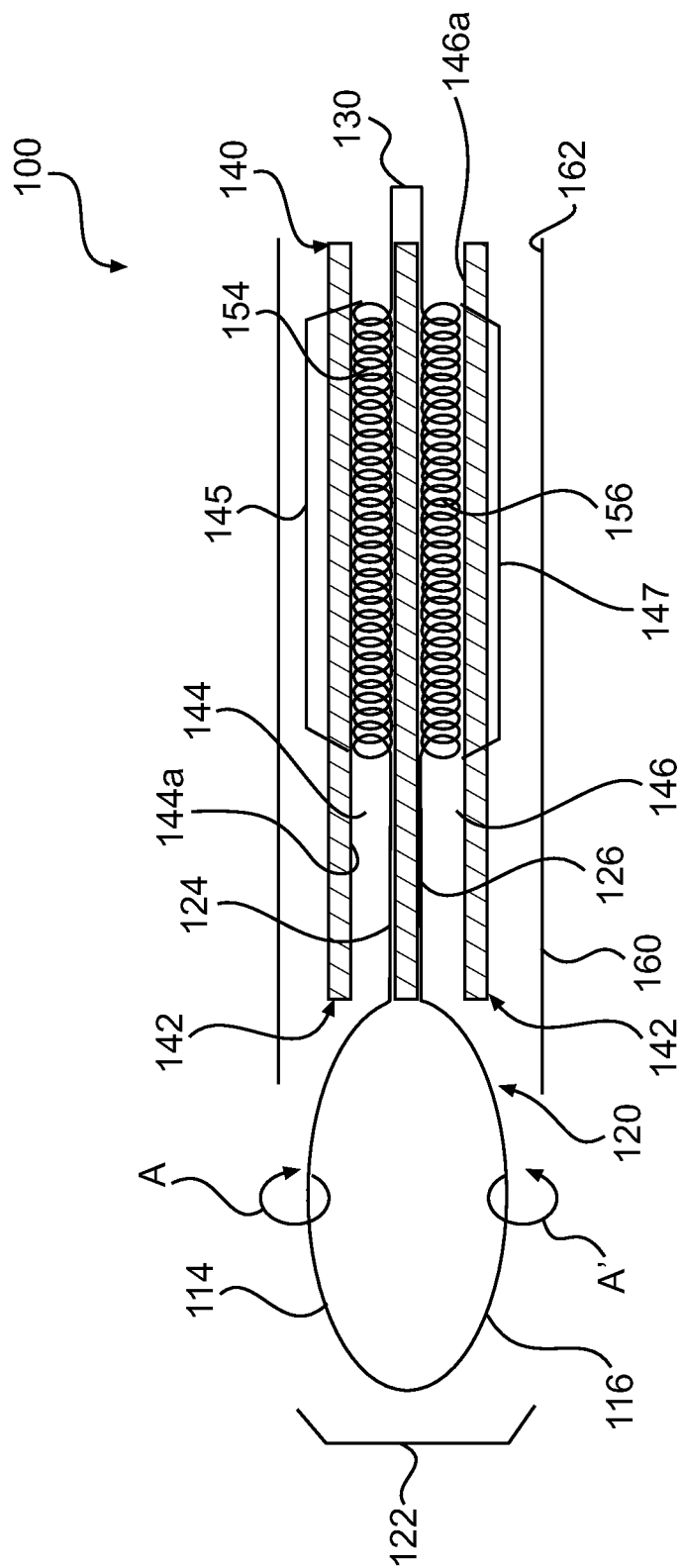
FIG. 1 is a schematic illustration of an exemplary medical device.

FIG. 1 is a schematic illustration of an exemplary medical device 100. The device 100 may include a snare element 120 and a delivery member 140. The snare element 120 may include a snare loop 122 extending distally from first and second snare legs 124 and 126. The snare element 120 may be made of a single continuous, e.g., monolithically formed, piece of material such as wire 130. Alternatively, the snare element 120 may be made of multiple members, e.g. wires, fused together. Each of the first and second snare legs 124 and 126 may extend to a proximal portion (not shown) of medical device 100 where the snare legs 124 and 126 may be associated with any appropriate user interface such as, for example, a handle (not shown). The handle may be configured to remain outside of the patient's body during a procedure and may allow a user to control the snare element 120, for example, by applying an axially directed pushing or pulling force on one or both of the first and second snare legs 124 and 126.

The snare element 120 may be coupled to a source of energy (not shown) such as, for example, an electrosurgical generator through any appropriate means. For example, one or both of the first and second snare legs 124 and 126 may be electrically coupled to the electrosurgical generator to cauterize tissue during a procedure. It is understood, however, that one or more portions of the snare element 120 may be insulated to prevent unintended damage to surrounding tissue. Upon connection of the snare element 120 to a source of energy, the user may control the electric current that passes through the snare element 120 to assist in cutting and/or coagulation of body tissues. The snare element 120 may also tighten around the target tissue (not shown) and apply mechanical force to aid in cauterization.

The snare element 120 may be formed of any appropriate material sufficient to maintain flexibility and columnar strength during operations. Additionally, the snare element 120 may be formed of a material configured to conduct electrical energy sufficient to cauterize tissue. In some embodiments, the wire 130 of the snare element 120 may be a monofilament wire or a multifilament wire. Multiple filaments within the wire 130 may be twisted, braided, crimped and/or otherwise bonded together. The wire 130 may be formed using any suitable biocompatible material such as, but not limited to metals, alloys, or the like. Exemplary materials include steel, tungsten, Nitinol™, or titanium. In addition, the loop 122 may be configured to have any suitable shape such as, but not limited to, circular, oval, hexagonal, rectangle, square, irregular, polygonal, semicircular, or the like.

In some embodiments, the snare element 120 including the loop 122 and the legs 124 and 126 may be formed as a unitary structure. However, in other embodiments, the legs 124 and 126 may be discreetly formed and later connected to the loop 122 using any suitable technique known in art such as, for example, welding, soldering, and/or heat bonding.

As will be described in greater detail below, the snare element 120, particularly the snare loop 122, may be configured to effectively grip tissue for capturing and cauterization of the target tissue. In addition, the surface of the legs 124 and 126 may be configured to smoothly and easily pass through the delivery element 140. In some embodiments, the wire 130 of the snare element 120 may contain a plurality of micro-features (not shown in FIG. 1) and/or adhesive coatings (not shown). Exemplary micro-features and adhesive coatings will be discussed with reference to subsequent figures.

As shown in FIG. 1, the device 100 may include a delivery member 140. Delivery member 140 may be configured to pass snare element 120 therethrough. For example, in a first retracted configuration, snare element 120 may be axially retracted (e.g., proximally pulled) into delivery member 140 such that the snare loop 122 is prevented from deploying distally of the delivery member 140. That is, wire 130 of the loop 122 may be snuggly received against the distal end surface of delivery member 140, such that loop 122 is compressed. Upon actuation, however, snare element 120 may be axially advanced (e.g., distally pushed) away from delivery member 140 and into a second expanded configuration (FIG. 1).

The delivery member 140 may be configured to be received within a channel 162 of a moveable sheath and/or a luminal introducer device 160 such as an endoscope, catheter, etc. During a procedure, a physician may navigate the luminal introducer device 160 toward the target tissue (not shown). After navigation of the luminal introducer device 160, delivery member 140 may be passed through the channel 162 so as to position a distal end portion 142 of delivery member 140 adjacent to the target tissue while the snare element 120 is in the retracted configuration. Alternatively, delivery member 140 may be navigated toward the target tissue without the luminal introducer device 160, or concurrently with the luminal introducer device 160. Upon reaching the target tissue, the snare element, e.g., the snare loop 122, may be expanded distally from the distal end portion 142 of delivery member 140.

The delivery member 140 may have two lumens, a first lumen 144 and a second lumen 146 for receiving respective one of the two legs 124 and 126 of the snare element 120. Each of the first and second lumens 144 and 146 may terminate at distal end portion 142. A rotational element 154 and 156 may be located within each lumen 144 and 146, respectively. The rotational element 154 within the first lumen 144 may be oriented in first direction whereas the rotational element 156 within the second lumen 146 may be oriented in a second direction. In an exemplary embodiment, the first direction may be opposite that of the second direction. For example, the first rotational element 154 may be right-handed, while the second rotational element 156 may be left-handed. In some embodiments, the first rotational element 154 may be configured to impart clock-wise rotational motion to the first leg 124 and the second rotational element 156 may be configured to impart counter clock-wise rotational motion to the second leg 126.

The rotational elements 154 and 156 may be configured to convert linear motion into rotational motion of the snare element 120. For example, first leg 124 may be received within the first rotational element 154. During use, axial movement of the snare element 120, and thereby the first leg 124 may result in the coiling (e.g., turning and/or rotating) of at least a portion of the first leg 124, e.g. wire spiral 145. Likewise, second leg 124 may be received within the second rotational element 156. During use, axial movement of the snare element 120, and thereby the second leg 126 may result in the coiling (e.g., turning and/or rotating) of at least a portion of the second leg 126, e.g. wire spiral 147. In one exemplary embodiment, when a user pushes or pulls (or applies a linearly directed force) on the proximal end (not shown) of the snare element 120 via a handle or other suitable interface, the first spiral 145 may rotate clock-wise within the first lumen 144, while the second spiral 147 may rotate counter clock-wise within the second lumen 146. It is understood, however, that in another embodiment, rotational elements 154 and 154 may be configured so as to impart first spiral 145 to rotate counter clock-wise within the first lumen 144, and second spiral 147 to rotate clock-wise within the second lumen 146. As shown in FIG. 1, the first side 114 of the loop 122 that is connected to the first leg 124 may rotate in a clock-wise direction (A), while the second side 116 of the loop 122 that is connected to the second leg 126 may rotate in a counter clock-wise direction (A'). The rotational motion of the first and second sides 114 and 116 may be a partial rotation, a single complete rotation, and/or multiple complete rotations.

In embodiments employing a sheath or luminal introducer device 160, the delivery member 140 may be contained within the channel 162 of the luminal introducer device 160. In such an embodiment, instead of, or in addition to applying an axially directed force on snare element 120, a user may cause rotational motion of the first and second sides 114 and 116 of the loop 122 by applying a linear force on the luminal introducer device 160 to move the luminal introducer device 160. For example, when the outer dimension (e.g., diameter) of the snare loop 122 is greater than the outer dimension (e.g., diameter) of the luminal introducer device 160, a user may distally push luminal introducer device 160 relative to snare element 120 so as to urge snare element 120 toward the first retracted configuration. As snare element 120 moves toward the first retracted configuration, first leg 124 may rotate about rotational element 154 in first lumen 144, whereas second leg 126 may rotate about rotational element 156 in second lumen 146. Alternatively, pulling on the luminal introducer device 160 proximally relative to snare element 120 may cause the snare element 120 to move into an expanded configuration forming snare loop 122. During this configuration change, the first and second legs 124 and 126 may rotate about rotational elements 154 and 156, respectively.

Likewise, delivery member 140 may manipulated to impart rotational motion to the first and second legs 124 and 126 about rotational elements 154 and 156. In such an embodiment, instead of, or in addition to applying an axially directed force on snare element 120, a user may cause the rotational motion of the first and second sides 114 and 116 of the loop 122 by applying a linear force on delivery member 140. For example, when the outer dimension (e.g., diameter) of the snare loop 122 is greater than the outer dimension (e.g., diameter) of the delivery member 140, a user may distally push delivery member 140 relative to snare element 120 so as to urge snare element 120 toward the first retracted configuration. As snare element 120 moves toward the first retracted configuration, first leg 124 may rotate about rotational element 154 in first lumen 144, whereas second leg 126 may rotate about rotational element 156 in second lumen 146. Alternatively, pulling the delivery member 140 proximally relative to snare element 120 may cause the snare element 120 to move into an expanded configuration forming snare loop 122. During this configuration change, the first and second legs 124 and 126 may rotate about rotational elements 154 and 156, respectively.

The rotational elements 154 and 156 may be positioned at various locations along the length of the lumens 144 and 146. For example, the rotational elements 154 and 156 may be positioned proximate (e.g., near) the distal end portion 142 of the lumens 144 and 146 so as to provide localized rotation to the loop 122. The axial length of rotational elements 154 and 156 may also vary. In some embodiments, the rotational elements 154 and 156 may extend along the entire length of lumens 144 and 146 or they may extend along a portion of the length of each lumen 144 and 146, where the length is less than the entire length of the lumens 144 and 146. As shown, each of rotational elements 154 and 156 may include a plurality of helical turns. However, in an alternative exemplary embodiment, each of rotational elements 154 and 156 may include only a single helical turn.

In one exemplary embodiment, rotational element 154 may include a helical female thread or groove on the inner wall 144a of the first lumen 144. Additionally, rotational element 156 may include a helical female thread or groove on the inner wall 146a of second lumen 146. Alternatively, each of the rotational elements 154 and 156 may include a helical mandrel positioned within each of the first lumen 144 and the second lumen 146 along which the wire 130 forms the spirals 145 and 147. Each mandrel may have grooves on its outer surface and the legs 124 and 126 may travel around those grooves to cause rotational motion of the first and second sides 114 and 116 (not shown).

FIG. 2 is a cut-away view of exemplary rotational elements 154 and 156 within the lumens 144 and 146 of the delivery member 140. As shown, the first lumen 144 may have a right-handed female helical thread or groove 164 and the second lumen 146 may have a left-handed female helical thread or groove 166. For example, the grooves 164 and 166 may be right and left-handed female screw threads that have been machined (e.g., threaded) on the inner walls 144a and 146a of the lumens 144 and 146, respectively. Any appropriate machining technique such as drilling, grinding, turning, etching, and/or the like may be used to create grooves 164 and 166. In some cases, molding techniques may also be utilized.

FIG. 3 is a schematic illustration of an exemplary medical device 100 in use. For example, as shown in FIG. 3, rotation of the first and second sides 114 and 116 can be achieved as described above. That is, rotation may be achieved via an axially-directed force to the first and second legs 124 and 126, an axially directed force to an optional moveable sheath and/or a luminal introducer device 160, and/or an axially-directed force to the delivery member 140. Upon application of such a force, snare loop 122 may be caused to transition between (1) one of the first retracted position and the second expanded configuration (FIG. 1), and the (2) other of the first retracted position and the second expanded configuration.

For example, during operation, a user may cause the loop 122 (shown as having a circular cross-section with sides 114 and 116), in the first retracted configuration, to be advanced past the distal end portion 142 of the lumens 144 and 146 so as to transition into the second expanded configuration (FIG. 1). In the second expanded configuration, the loop 122 may be placed about target tissue 180 for resection. Once placed about target tissue 180, the user may move the legs 124 and 126 proximally relative to the delivery member 140 and/or luminal introducer device 160 toward the delivery member 140, which may in turn partially retract or tighten the loop 122 around the target tissue 180. As the legs 124 and 126 of the snare are pulled proximally, the wire 130 may be moved into and through rotational elements 154 and 156, thereby inducing rotation of the first side 114 in a counter clock-wise direction (A) and the second side 116 in a clock-wise direction (A') as discussed with reference to FIG. 1. Additionally, as the legs 124 and 126 are proximally moved relative to the delivery member and/or luminal introducer device 160, the snare loop 122 is reduced in size as it is pulled into one or both of delivery member 140 and luminal introducer device 160 so as to urge the sides 114 and 116 of the snare loop 122 toward each other in the directions B and B' as shown so as to sever target tissue 180. Accordingly, target tissue 180 within snare loop 122 is resected. During resection, rotational motion of the first and second sides 114 and 116 increases a user's grip, and therefore, control of the target tissue.

In an embodiment in which the snare element is coupled with a source of energy, rotational motion of the first and second sides 114 and 116 may promote precise electrosurgical resection of target tissue 180. As described above, rotational motion of the first and second sides 114 and 116 increases a user's grip, and therefore, control of the target tissue so as to aid electrosurgical resection. Additionally, as the energized loop rotates, it may continuously cauterize the target tissue 180 thereby reducing bleeding and promoting a faster healing response.

For better control and improved grip, the device 100 may be designed to form a tissue interlock with the target tissue. In this context, tissue interlock refers to the frictional engagement, griping, or other like engagement of the tissue by the device 100, specifically the snare loop 122, via forces such as Van der Waals forces. In some embodiments, the tissue interlock may be formed and enhanced by a) an adhesive coating and/or b) a plurality of micro-features on the wire 130 of the snare element 120.

In some embodiments, an adhesive coating (not shown) extends along at least a portion of the snare element 120 to establish and/or enhance tissue interlock during placement or tightening of the snare element 120 about the target tissue 180. Exemplary coating materials include pressure sensitive adhesive (PSA) material and mucoadhesive material. PSA is a class of materials whose adhesive properties are activated under pressure. PSA materials may be made from, for example, acrylics, rubbers, and silicones. Mucoadhesive materials, such as, for example, polymers with hydrogen bonding groups, are a class of materials that are naturally adhesive to mucosal tissue. Non-toxic biocompatible adhesives may be suitable for this application.

In some embodiments, a plurality of micro-features may be disposed on the surface of the wire 130 of the snare element 120 to establish and/or enhance tissue interlock. The micro-features also improve traction by increasing the surface area of the wire 130 that is in contact with the tissue. Micro-features are projections or protrusions that may have a dimension (e.g., length, width, or height) anywhere between about 1 and about 999 μm. Micro-features may be configured to enhance tissue interlock between the snare loop 122 and target tissue 180. For example, during operation, tissue may become lodged within crevices formed by the micro-features thereby improving the grip of the device 100 to the target tissue 180.

In some embodiments, the micro-features may be disposed throughout the entire length of the wire 130 of the snare element 120. In other embodiments, the micro-features may be disposed only on the portion of the wire 130 comprising the loop 122. In some embodiments, the micro-features may be present only in selected portions of the loop 122 such as the sides 114 and 116. In some embodiments, the micro-features may be disposed on the first and second legs 124 and 126 (FIG. 1) or any other portion of the wire 130 that passes through the rotational elements 154 and 156. It is understood that the presence of these micro-features within the rotational elements 154 and 156 may increase lubricity (e.g., the smooth movement) of the wire 130 within and about the rotational elements 154 and 156 of the lumens 144 and 146. In some embodiments, the micro-features may be protrusions have a shape that is complementary to rotational elements 154 and 156.

Figure 4A:
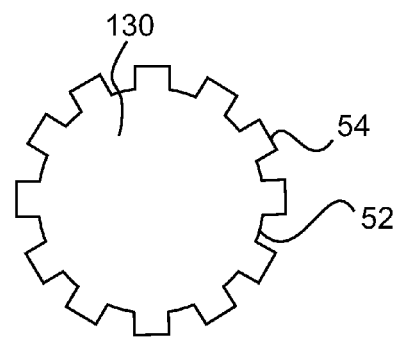
FIGS. 4A-4C, 5A-5D and 6A-6J show exemplary micro-features on embodiments of the snare element.
Figure 4B:
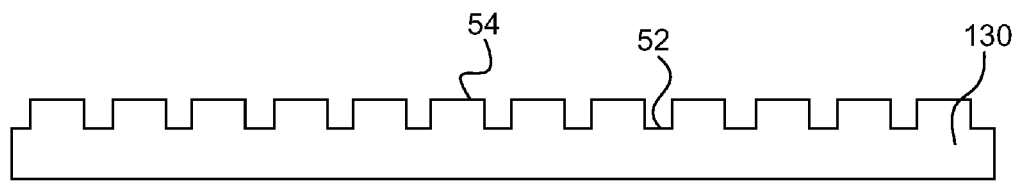
Figure 4C:
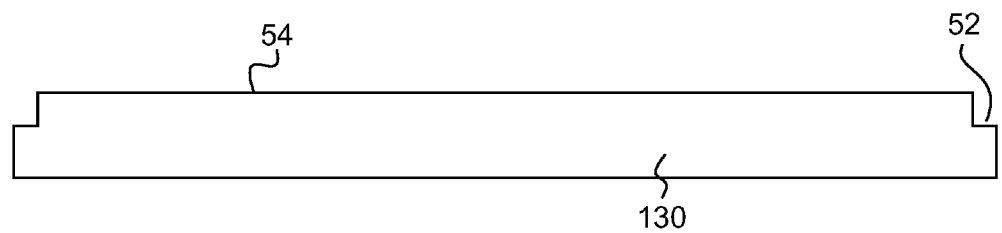

Variations in the structure of the micro-features have been contemplated. FIGS. 4A, 4B and 4C show exemplary micro-features 54 on the wire 130 of the snare element 120 (not shown). For example, FIG. 4A depicts a cross-sectional wire 130 which may have an external circumferential wall or base 52 from which one or more micro-features 54 extend radially outward. FIGS. 4B and 4C show alternate longitudinal views of the wire 130. In some embodiments, the micro-features may include discrete features along the length of the wire 130 as shown in FIG. 4B. In other embodiments, the micro-features may include elongate ridges or protrusions along the length of the wire 130 as shown in FIG. 4C.

Figure 5A:
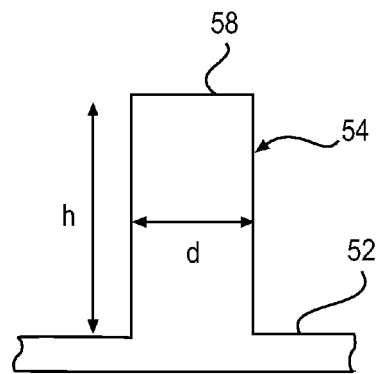
Figure 5B:
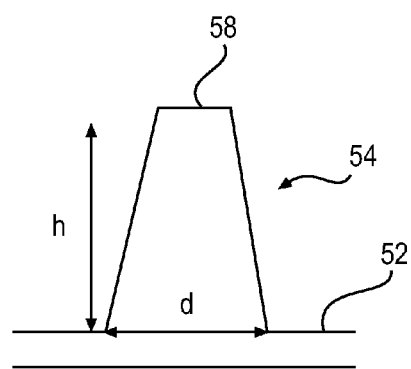
Figure 5C:
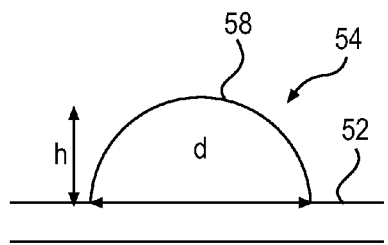
Figure 5D:
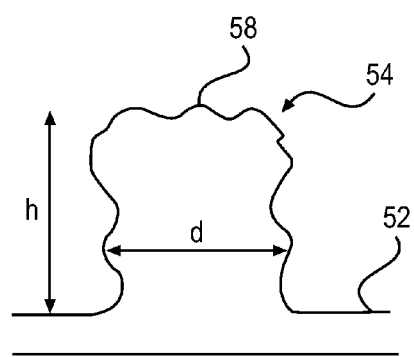

FIGS. 5A-5D show side views of exemplary micro-features 54, which protrude from the base 52 to a peak 58. Each micro-feature 54 may have a height h extending between the base 52 and the peak 58. Additionally, each micro-feature 54 may have a dimension d (e.g., diameter and/or width). In some embodiments, the micro-features may be cylinders (FIG. 5A), prisms with a rectangular or polygonal base (FIG. 5B), bumps (FIG. 5C), or have non-traditional shapes with a plurality of bumps and/or ridges on multiple surfaces that do not define a cross-section that is circular, square, polygonal, etc. (FIG. 5D).

Figure 6A:
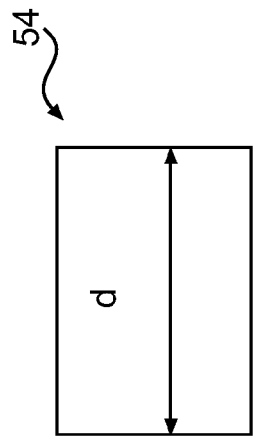
Figure 6B:
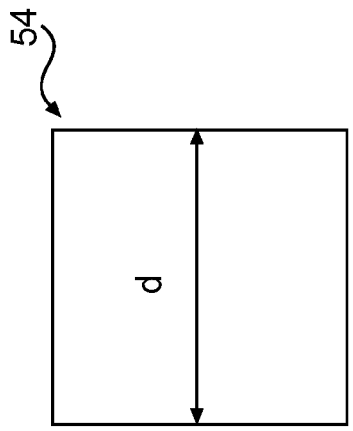
Figure 6C:
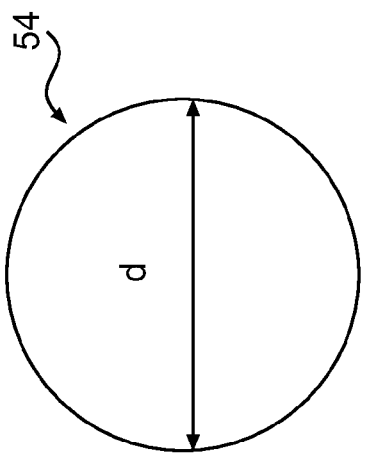
Figure 6E:
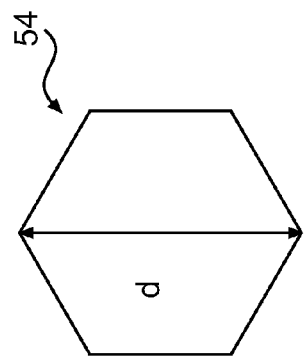
Figure 6G:
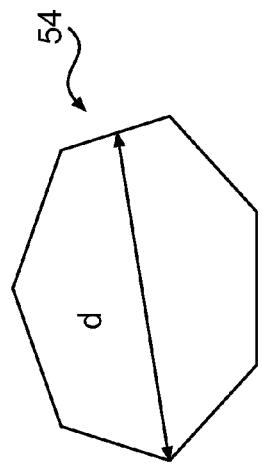
Figure 6D:
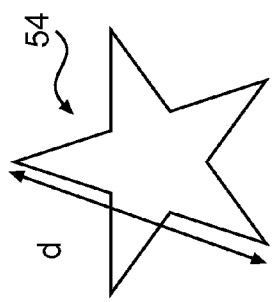
Figure 6F:
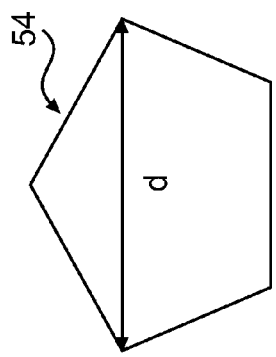
Figure 6J:
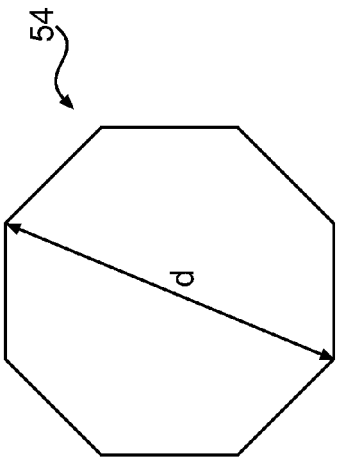
Figure 6I:
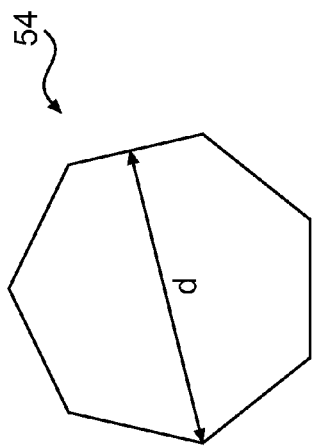
Figure 6H:
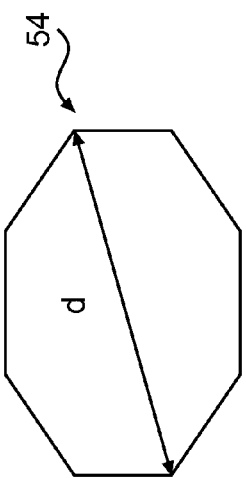
Figure 7B:
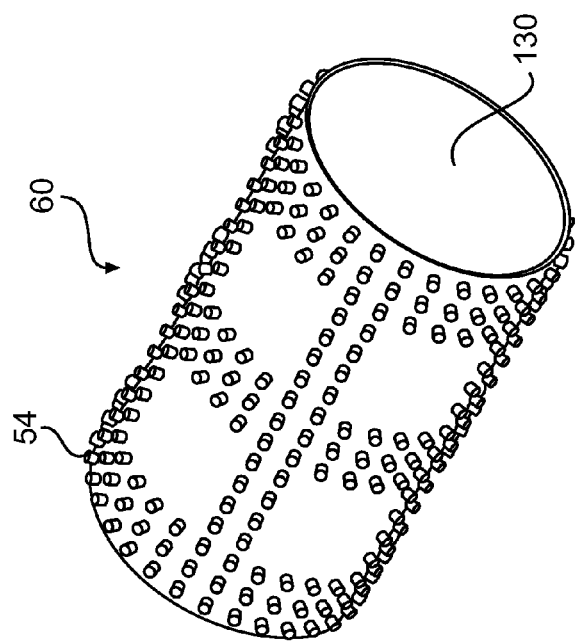
Figure 7A:
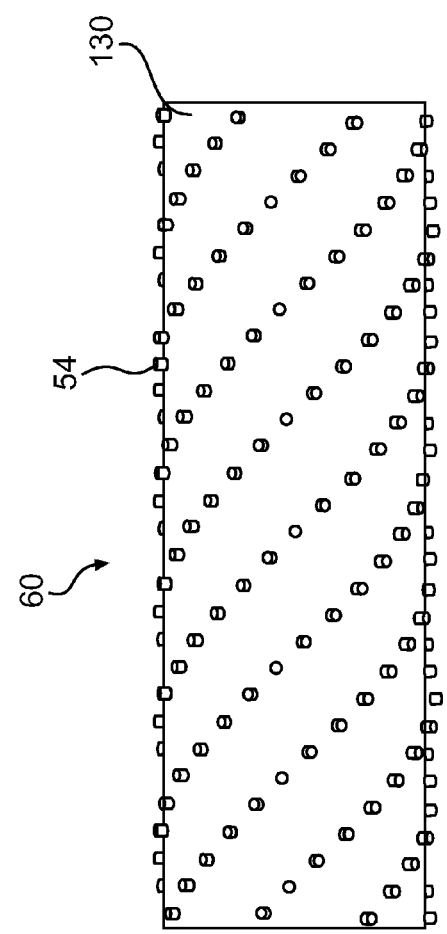

Each micro-feature 54 may have various cross-sectional shapes including circular (FIG. 6A), square (FIG. 6B), rectangular (FIG. 6C), star-shaped (FIG. 6D), hexagonal (FIG. 6E), pentagonal (FIG. 6F), heptagonal (FIG. 6G), octagonal (FIG. 6H), nonagonal (FIG. 6I), decagonal (FIG. 6J), other polygonal, or non-traditional cross-sections. The polygonal cross-sections may have sides of equal length or unequal lengths. Embodiments of the present disclosure contemplate multiple micro-features 54 of multiple cross-sectional shapes including traditional shapes (e.g., circles, squares, rectangles, hexagons, polygons, etc.) and non-traditional shapes having a perimeter where at least a portion of the perimeter is curvilinear. In at least one embodiment, the micro-features 54 may be solid (e.g., filled) structures, but in other embodiments, micro-features 54 may be hollow structures. In some embodiments, each micro-feature 54 may have a constant cross-section, but in other embodiments the micro-features 54 may have variable cross-sections.

In some embodiments, the plurality of micro-features 54 may be arranged in one or more micro-pattern(s) 60. The micro-pattern 60 may affect the strength of the tissue interlock between the wire 130 (not shown) and the target tissue 180. In some embodiments, the micro-features 54 within a micro-pattern 60 may have different shapes. In some embodiments, the peaks 58 of micro-features 54 may be shaped to improve tissue interlock. In some embodiments, the ends can be tapered, pointed, rounded, concave, jagged, or frayed to form barbs, conical protrusions, and/or teeth. In some embodiments, the micro-features 54 may be spaced apart equidistantly in the micro-pattern 60. Exemplary micro-patterns 60 composed of the micro-features 54 on the wire 130 are shown in FIGS. 7A, 7B and 8A-8C. The micro-features 54 of the micro-pattern 60 may be arranged in a spiral array (FIG. 7A), a square grid pattern (FIG. 7B), a rectangular array, a square array (FIG. 8A), a polygonal array with a central micro-feature (FIG. 8B) and a polygonal array without a central micro-feature (FIG. 8C). In some embodiments, the micro-pattern 60 may have rows and columns that are not perpendicular to each other. The shapes and configurations of the micro-features 54 and micro-patterns 60 discussed here are exemplary in nature, and for a person it is understood that various other cross sectional shapes may also be contemplated.

Figure 9A:
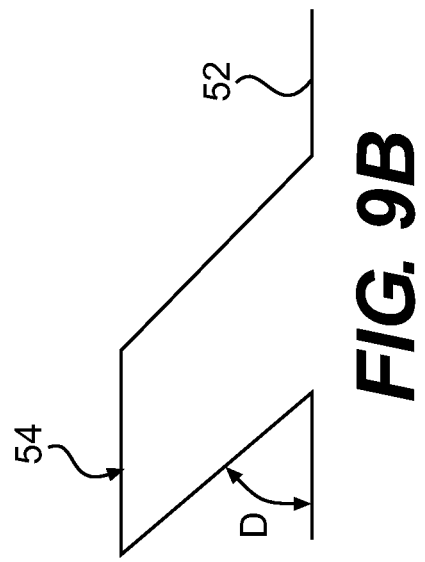
FIGS. 9A and 9B show exemplary directional micro-features on embodiments of the snare element.
Figure 9B:
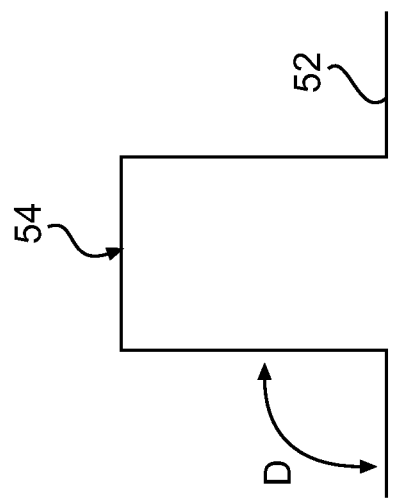

To create a directional grip on the tissue, the micro-features 54 in the micro-pattern 60 may be designed to be directional. FIG. 9A is a side view of a micro-feature 54 that is non-directional, where the angle (D) between the base 52 and a side wall 50 is a right-angle. In contrast, micro-feature 54 is directional if the angle D between the side wall 50 to the base 52 is non-perpendicular. FIG. 9B shows a micro-feature 54 with the angle D, which is less than 90°. For example, as shown in FIG. 9B, angle D may be approximately 45°. It is understood that directional micro-features 54 may have a stronger grip on the tissue because it will be harder to dislodge the tissue from the angled crevices formed between the side wall 50 and the base 52. Additionally, since tissue in different regions of the body, e.g. the upper GI tract and the colon exhibit different properties, it is understood that the angle D can be chosen to enhance gripping in that particular area.

Micro-features 54 may be made from any material (such as steel, tungsten, Nitinol™, or titanium, PSA materials) that can be micro-machined or created on the surface using techniques such as etching, hot-melting, etc. In some embodiments, the wire 130 may be coated with an adhesive coating and then micro-features 54 may be machined into the coating. In other embodiments, the micro-features 54 can be first machined onto the wire 130 and then coated with the adhesive coating. The adhesive coating may be made on the wire using any technique known in the art such as spraying, dipping and the like. Micro-patterns 60 of micro-features 54 may be created by using techniques like grinding, turning, etching or the like.

Figure 10A:
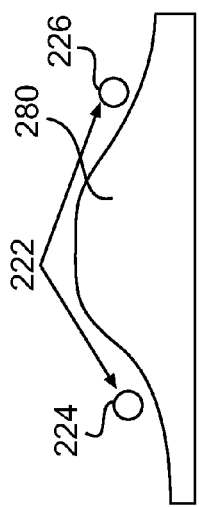
FIGS. 10A-10C are schematic illustrations depicting an exemplary medical device in operation, according to an embodiment of the present disclosure.
Figure 10B:
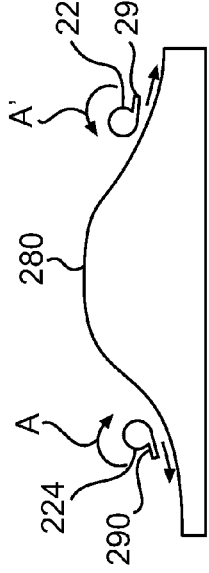
Figure 10C:
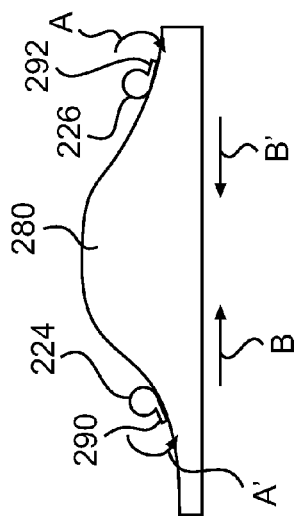

In some embodiments, the micro-features may include selectively deployable flaps 290 and 292 (see FIGS. 10B and 10C). The flaps 290 and 292 may be spring-loaded or may be made of shape memory alloy, e.g., Nitinol™. The flaps 290 and 292 may be wound around the circumference of the sides 224 and 226 in a closed configuration (see FIG. 10A). The flaps may be biased to be in open configuration so that when the user rotates the sides 224 and 226 in one direction to unwind the flaps 290 and 292, the flaps 290 and 292 open and stay open after subsequent rotation in the opposite direction (see FIG. 10C).

Various methods for operating the disclosed medical devices may be used. One method for operating medical device 200 is illustrated in FIGS. 10A-10C. As shown in FIG. 10A, a snare loop 222 (shown as cross-sections of sides 224 and 226) may be deployed about the tissue of a patient (i.e., the target tissue 280). The user may initiate rotation of the first side 224 in a clock-wise direction (A') and the second side 226 in a counter clock-wise (A) direction by applying a linear force on the proximal end of the snare element (not shown) as depicted in FIG. 10B. The linear force may be converted to rotational motion via first and second rotational elements 154 and 156 as described above. As a result, selectively deployable flaps 290 and 292 with or without adhesive coating (not shown), open to better grip the target tissue 280. The flaps 290 and 292 in open position may have increased surface area, thereby improving adhesion between the tissue and the loop 222.

The user may then rotate the loop 222 in the opposite direction such that side 224 in a counter clock-wise direction (A) and side 226 in a clock-wise direction (A'). As a result, the target tissue 280 is effectively gripped and move towards the center of the loop 222 along directions B and B'. While the steps illustrated above may provide a method for operating the disclosed medical device 200 for effectively gripping tissue, variations are also contemplated to these methods for achieving the same or a similar goal.

Subsequently, the target tissue 280 may be cut either by mechanical force or by using electro-cauterization along the loop 222. The severed tissue (not shown) may be released into the body lumen or retrieved and/or removed by other medical devices such as, for example, forceps, or a basket. The loop 222 may be retracted into the delivery member (not shown) and can exit the body lumen via a luminal introductory device or the like.

Using the exemplary methods described above, the device 200 may be used for removal of undesired tissue such as lesions from a patient's body for treatment or diagnostic purposes. The device 200 may be a single-use device which can be discarded after one use.

Other embodiments of the present disclosure will be apparent to those skilled in the art after consideration of the specification and practice of the embodiments disclosed herein. It is intended that the specification and examples be considered as exemplary only, with a true scope and spirit of the invention being indicated by the following claims.

What is claimed is:

1. A medical device, comprising:
   a delivery member having at least two lumens extending therethrough, each lumen of the at least two lumens including a rotational element therein, wherein each rotational element is configured to convert linear motion into rotational motion to expand or retract a snare element; and
   the snare element including a distal snare loop and two proximally extending legs, wherein each leg is within one of the at least two lumens;
   wherein the rotational element in a first lumen of the at least two lumens is configured to impart a clock-wise rotation to a first leg of the two proximally extending legs, wherein the rotational element in a second lumen of the at least two lumens is configured to impart a counter clock-wise rotation to a second leg of the two proximally extending legs, and wherein the rotational element in each of the at least two lumens includes at least one of a female helical groove and a helical mandrel.

2. The medical device of claim 1, further comprising:
   a plurality of micro-features extending radially outwardly from the snare element.

3. The medical device of claim 2, wherein at least one of the plurality of micro-features extends at an angle non-perpendicular to a base of the snare element.

4. The medical device of claim 2, wherein at least one of the plurality of micro-features is a selectively deployable flap.

5. The medical device of claim 1, further comprising:
   an adhesive coating extending along at least a portion of the snare element.

6. The medical device of claim 5, wherein the adhesive coating includes at least one of a pressure sensitive adhesive material and a mucoadhesive material.

7. The medical device of claim 5, wherein the adhesive coating is disposed on the snare loop.

8. A medical device, comprising:
   a delivery member having at least two lumens extending therethrough, each lumen of the at least two lumens including a rotational element therein, wherein each rotational element is configured to convert linear motion into rotational motion to expand or retract a snare element; and
   the snare element including a distal snare loop and two proximally extending legs, wherein each leg is within one of the at least two lumens;
   wherein the snare loop includes a first side wire portion and a second side wire portion opposite the first side wire portion on opposite sides of a longitudinal axis of the snare element, wherein application of an axial force to the proximally extending legs causes clock-wise rotation of the first side wire portion about an axis of the first side wire portion and causes counter clock-wise rotation of the second side wire portion about an axis of the second side wire portion, and wherein the rotational element in each of the at least two lumens includes at least one of a female helical groove and a helical mandrel.

9. The medical device of claim 8, further comprising:
   a plurality of micro-features extending radially outwardly from the snare element.

10. The medical device of claim 9, wherein at least one of the plurality of micro-features includes a selectively deployable flap.

11. The medical device of claim 8, further comprising:
    an adhesive coating extending along at least a portion of the snare element, wherein the adhesive coating includes at least one of a pressure sensitive adhesive material and a mucoadhesive material.

12. The medical device of claim 8, wherein the rotational element in a first lumen of the at least two lumens has a right-handed thread or groove, and wherein the rotational element in a second lumen of the at least two lumens has a left-handed thread or groove.

13. A method of operating a medical device, comprising:
    deploying a snare about tissue of a patient, wherein the snare includes a delivery member having at least two lumens extending therethrough, each lumen of the at least two lumens including a rotational element therein, wherein the rotational element in each of the at least two lumens includes at least one of a female helical groove and a helical mandrel, wherein each rotational element is configured to convert linear motion into rotational motion, and a snare element including a distal snare loop and two proximally extending legs, wherein each leg is within one of the at least two lumens, wherein the snare loop includes a first side wire portion and a second side wire portion opposite the first side wire portion on opposite sides of a longitudinal axis of the snare element;
    applying an axially directed force so as to impart clock-wise rotation of the first side wire portion about an axis of the first side wire portion and counter clock-wise rotation of the second side wire portion about an axis of the second side wire portion to expand or retract the distal snare loop.

14. The method of claim 13, further comprising:
    engaging tissue via a plurality of micro-features extending radially outwardly from the snare element.

15. The method of claim 14, wherein engaging includes forming a directional engagement with tissue, wherein at least one of the plurality of micro-features extends at an angle non-perpendicular to a base of the snare element.

16. The method of claim 13, wherein the applying includes pulling on a proximal end of the legs or moving a sheath disposed about the loop proximally.

17. The method of claim 13, wherein the snare element includes an adhesive coating extending along at least a portion of the snare element, the adhesive coating including at least one of a pressure sensitive adhesive material and a mucoadhesive material.

\* \* \* \* \*